United States Patent [19]

Vu et al.

[11] Patent Number: 5,725,846
[45] Date of Patent: Mar. 10, 1998

[54] CLEAR ANTIPERSPIRANT STICK CONTAINING DIBENZYLIDENE ALDITOL AND HYDROXYALKYL CELLULOSE

[75] Inventors: Tuan M. Vu, Brighton; Carl F. Iovanni, Cambridge; Jayant N. Sane, Framingham, all of Mass.

[73] Assignee: The Gillette Company, Boston, Mass.

[21] Appl. No.: 588,618

[22] Filed: Feb. 6, 1996

Related U.S. Application Data

[63] Continuation-in-part of Ser. No. 397,450, Mar. 2, 1995, abandoned, which is a continuation of Ser. No. 695,839, Jul. 10, 1996, Pat. No. 5,705,171.

[51] Int. Cl.⁶ ............... A61K 7/32; A61K 7/34; A61K 7/36; A61K 7/38
[52] U.S. Cl. ............... 424/65; 424/66; 424/67; 424/68; 424/401
[58] Field of Search ............... 424/65, 66, 68, 424/401

[56] References Cited

U.S. PATENT DOCUMENTS

| | | | |
|---|---|---|---|
| H1473 | 8/1995 | Orofino et al. | 424/67 |
| 3,981,986 | 9/1976 | Rubino | 424/47 |
| 4,017,599 | 4/1977 | Rubino | 424/47 |
| 4,154,816 | 5/1979 | Roehl et al. | 424/68 |
| 4,346,079 | 8/1982 | Roehl | 424/65 |
| 4,383,988 | 5/1983 | Teng et al. | 424/68 |
| 4,518,582 | 5/1985 | Schamper et al. | 424/66 |
| 4,719,102 | 1/1988 | Randhawa et al. | 424/66 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,743,444 | 5/1988 | McCall | 424/65 |
| 4,781,917 | 11/1988 | Luebbe et al. (I) | 424/65 |
| 4,816,261 | 3/1989 | Luebbe et al. | 424/65 |
| 4,822,602 | 4/1989 | Sabatelli | 424/65 |
| 4,948,578 | 8/1990 | Burger et al. | 424/68 |
| 4,954,333 | 9/1990 | Ward | 424/66 |
| 5,106,999 | 4/1992 | Gardlik et al. | 549/364 |
| 5,162,378 | 11/1992 | Guthauser | 514/785 |
| 5,200,174 | 4/1993 | Gardlik et al. | 424/66 |
| 5,270,034 | 12/1993 | Cheng | 424/68 |
| 5,286,755 | 2/1994 | Kauffmann et al. | 514/944 |
| 5,346,694 | 9/1994 | Juneja | 424/66 |
| 5,368,848 | 11/1994 | Brazinsky et al. | 424/65 |
| 5,376,363 | 12/1994 | Benfatto et al. | 424/66 |
| 5,405,605 | 4/1995 | Shin | 424/68 |
| 5,463,098 | 10/1995 | Giovanniello et al. | 556/27 |
| 5,490,979 | 2/1996 | Kasat et al. | 424/66 |
| 5,516,511 | 5/1996 | Motley et al. | 424/65 |
| 5,585,092 | 12/1996 | Trandai et al. | 424/65 |

FOREIGN PATENT DOCUMENTS

| | | |
|---|---|---|
| 0 260 030 B1 | 8/1987 | European Pat. Off. . |
| 0 260 030 B1 | 6/1988 | European Pat. Off. ......... A61K 7/32 |
| 0260030B1 | 6/1988 | European Pat. Off. . |
| 0 404 532 A1 | 12/1990 | European Pat. Off. ......... A61K 7/32 |
| WO 91/15191 | 10/1991 | WIPO ............... A61K 7/38 |

OTHER PUBLICATIONS

Klepak, "Antiperspirants take a clear lead", *Manufacturing Chemist* (Nov. 1994), pp. 31–36.
Disorbene, Roquette product brochure (1992).

*Primary Examiner*—Joseph L. Schofer
*Assistant Examiner*—Sharon Howard
*Attorney, Agent, or Firm*—Stephan P. Williams

[57] ABSTRACT

A clear gel cosmetic stick includes a liquid vehicle, a dibenzylidene alditol as a gelling agent, an antiperspirant salt dissolved in the liquid vehicle, and a hydroxyalkyl cellulose co-gellant. The cosmetic stick comprises in percent by weight about 70% to about 95%, preferably 75 to 92%, of a liquid vehicle comprising a polyhydric alcohol having from 3 to 6 carbon atoms and from 2 to 6 hydroxyl groups, about 0.5% to about 1.5%, preferably 0.7% to 1.3%, of a dibenzylidene alditol, about 3% to about 22%, preferably 6% to 15%, of an antiperspirant salt dissolved in said vehicle, and about 0.1% to about 0.5%, preferably 0.2% to 0.4%, of a hydroxyalkyl cellulose. Preferably the liquid vehicle is substantially free of monohydric alcohol and is also substantially free of strong alkali such as NaOH and KOH. Preferably the cosmetic stick will have a pH greater than 4.4, more preferably greater than 4.7, a turbidity of less than about 120 NTU, more preferably less than 100 NTU, and a hardness of about 60 to 150. By lowering the dibenzylidene alditol level to 1.5% or lower, the clarity and odor characteristics of the stick are greatly improved. The hardness of the stick is maintained by the addition of the hydroxyalkyl cellulose.

20 Claims, No Drawings

5,725,846

CLEAR ANTIPERSPIRANT STICK CONTAINING DIBENZYLIDENE ALDITOL AND HYDROXYALKYL CELLULOSE

CROSS-REFERENCE TO RELATED APPLICATION

This application is a continuation-in-part of application Ser. No. 08/397,450 filed on Mar. 2, 1995, now abandoned, which is a continuation of Ser. No. 08/695,839 on Jul. 10, 1996, now U.S. Pat. No. 5,705,171.

BACKGROUND OF THE INVENTION

The invention relates to clear gel cosmetic sticks which include a solubilized antiperspirant salt.

Gel antiperspirant sticks typically include a liquid vehicle, an antiperspirant salt, a gelling agent, and one or more emollients. Dibenzylidene alditols like dibenzylidene sorbitol (DBS), also known as dibenzylidene monosorbitol acetal (DBMSA), are one type of gelling agent that has been used in such sticks. Dibenzylidene alditols may degrade during manufacture and subsequent storage of the gel stick, in part because of the presence of the acidic antiperspirant salt in the stick. One product of the degradation, benzaldehyde, can provide an undesirable odor. Commercially available DBS gel antiperspirant sticks contain more than 2% DBS in order to have sufficient hardness. However, such sticks do not have optimum clarity or odor characteristics.

Various stabilizing agents have been incorporated into gel antiperspirant sticks containing dibenzylidene alditols in an effort to minimize dibenzylidene alditol degradation. Examples include sodium hydroxide, potassium hydroxide, sodium carbonate, zinc acetate, zinc oxide, zinc carbonate, potassium carbonate, diethanolamine, triethanolamine, disodium succinate, sodium benzoate, sodium octanoate, hexamethylenetetramine, urea, 2-amino-2-methyl-1-propanol, magnesium sulfate, calcium hydroxide, and N-(2-hydroxyethyl) acetamide. These and other stabilizing agents, although apparently effective to some degree in stabilizing the dibenzylidene alditol, may have other problems associated with them. Sodium hydroxide and potassium hydroxide, for example, may provide a composition with an undesirable odor.

SUMMARY OF THE INVENTION

The invention features a clear gel cosmetic stick that includes a liquid vehicle, a dibenzylidene alditol gelling agent, an antiperspirant salt, and a hydroxyalkyl cellulose co-gellant. The cosmetic stick comprises in percent by weight about 70% to about 95%, preferably 75% to 92%, of a liquid vehicle comprising a polyhydric alcohol having from 3 to 6 carbon atoms and from 2 to 6 hydroxyl groups, about 0.5% to about 1.5%, preferably 0.7% to 1.3%, of a dibenzylidene alditol, about 3% to about 22%, preferably 6% to 15%, of an antiperspirant salt dissolved in said vehicle, and about 0.1% to about 0.5%, preferably 0.2% to 0.4%, of a hydroxyalkyl cellulose. Preferably the liquid vehicle is substantially free of monohydric alcohol and is also substantially free of strong alkali such as NaOH and KOH. Preferably the cosmetic stick will have a pH greater than 4.4, more preferably greater than 4.7, a turbidity of less than about 120 NTU, more preferably less than 100 NTU, and a hardness of about 60 to 150. By lowering the dibenzylidene alditol level to 1.5% or lower, the clarity and odor characteristics of the stick are greatly improved. The hardness of the stick is maintained by the addition of the hydroxyalkyl cellulose.

DETAILED DESCRIPTION OF THE INVENTION

A "clear" gel stick, as used herein, is a stick that is visually clear so that, like glass, it allows ready viewing of objects behind it. Preferred clear gel sticks have a turbidity measurement, expressed in Nephelometric Turbidity Units (NTU) of less than 120 NTU, more preferably less than 100 NTU, and most preferably less than 80 NTU, when measured with a Hellige #965 Direct-Reading Turbidimeter. By "substantially free of off-odor" is meant that the gel stick (without any fragrance or fragrance masking agent) has an off-odor rating of 0 to 2, preferably 0 to 1, on a scale of 0 to 5 used by trained odor (or perfumery) experts, where 0 signifies no detectable off-odor and a rating of 4 to 5 is deemed unacceptable odor. By "stable" is meant that samples of the product, when stored at 45° C. for three months, will not exhibit any noticeable benzaldehyde odor or other off-odor (i.e. retains an odor rating of 0 to 2) and will not exhibit any significant change in clarity (i.e. retains a clarity of better than 120 NTU). Yellowness is measured by spectrophotometer absorbence at 408 nm with 0 corresponding to 0 ppm ferric chloride in water and 5 corresponding to 500 ppm ferric chloride in water.

The preferred clear gel sticks include a liquid vehicle, a dibenzylidene alditol gelling agent, an antiperspirant salt, a hydroxyalkyl cellulose, one or more emollients, and a fragrance. The liquid vehicle along with the gelling agents provide the matrix, or body, of the gel stick.

The liquid vehicle comprises a polyhydric alcohol having from 3 to 6 carbon atoms and from 2 to 6 hydroxyl groups. Such polyhydric alcohols include diethylene glycol, triethylene glycol, dipropylene glycol, 1,2-propylene glycol, 1,3-propylene glycol, 2-methyl-1,3-propanediol, 1,4-butylene glycol, 1,2-butylene glycol, 1,3-butylene glycol, 2,3-butylene glycol, 2,4-dihydroxy-2-methylpentane, glycerin, sorbitol and the like, and mixtures thereof. Preferred are 1,2-propylene glycol (normally referred to simply as propylene glycol), dipropylene glycol, 2-methyl-1,3-propanediol, 1,3-butylene glycol, sorbitol and mixtures thereof. Most preferred as the liquid vehicle is propylene glycol, which may optionally include one or more of the aforementioned polyhydric alcohols. While the liquid vehicle may optionally include a monohydric alcohol such as ethanol, it is preferred that the liquid vehicle be substantially free of monohydric alcohol. While the liquid vehicle may also optionally contain a co-solvent for the gelling agent (e.g. N-methyl pyrrolidone), as described in the prior art, such is not preferred.

The gel stick generally includes between about 70% and about 95%, preferably between about 75% and about 92%, of the liquid vehicle by weight. A stick including an insufficient quantity of the liquid vehicle may be unclear or may provide an inadequate support matrix for the remainder of the components. A stick including too much liquid vehicle may lack sufficient quantities of one or more of the other stick components.

The dibenzylidene alditol is the gelling agent. Examples include dibenzylidene sorbitol (DBS), dibenzylidene xylitol, and dibenzylidene ribitol. The aromatic rings in each benzylidene group may be unsubstituted or substituted, as described in U.S. Pat. No. 5,200,174, which is incorporated herein by reference. When substituted, it is preferred that the benzyl ring contain an electron withdrawing group at the meta position. Typical substituted compounds include di(meta-fluorobenzylidene) sorbitol and di(meta-chlorobenzylidene) sorbitol. The preferred gelling agent is dibenzylidene sorbitol (DBS).

For optimum clarity the gel stick should contain between about 0.5% and about 1.5%, preferably between about 0.7% and about 1.3%, of the dibenzylidene alditol by weight. If the gel stick includes too much of the dibenzylidene alditol, it may lack sufficient clarity and/or may have an undesirable odor. If the gel stick includes too little of the dibenzylidene alditol it may lack sufficient hardness. A particularly advantageous feature of the present invention is the use of low levels (i.e. 1.5% or less) of the dibenzylidene alditol gelling agent, which results in sticks of exceptional clarity and odor-free characteristics.

The gel stick also includes a hydroxyalkyl cellulose as an additional gelling agent (or co-gellant), which provides the stick with adequate hardness even when the stick includes only a low level of the dibenzylidene alditol. The combined use of the co-gellant with reduced amounts of the dibenzylidene alditol (i.e. amounts of 1.5% or less) enable the production of gel sticks of exceptional clarity and stability. The preferred hydroxyalkyl cellulose co-gellants include alkyl groups with between one and five carbon atoms. The preferred co-gellant is hydroxypropylcellulose (e.g. Klucel HFF, Aqualon). Preferred gel sticks include between about 0.1% and about 0.5%, preferably between about 0.2% and about 0.4%, of the hydroxyalkyl cellulose by weight.

Preferred gel sticks have a hardness of between about 60 and about 150 when measured on a TA-XT2 Texture Analyzer (Stable Micro System, Haste Hill, England). These hardness measurements correlate to the grams of force required for the standard arrowhead-type penetration needle to penetrate the stick a distance of 5 mm at 1 mm per second.

Antiperspirant salts which may be used in the gel sticks of the present invention include any of the conventional aluminum, zirconium and aluminum-zirconium salts known to be useful in antiperspirant compositions. These salts include aluminum halides and aluminum hydroxy halides (e.g., aluminum chlorohydrate), and mixtures or complexes thereof with zirconyl oxyhalides and zirconyl hydroxyhalides (e.g. aluminum-zirconium chlorohydrate).

Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 1.7 to about 12.5, most preferably about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine, typically with a Gly:Zr ratio of about 1:1 to 4:1.

It is especially preferred to utilize enhanced efficacy aluminum and aluminum-zirconium antiperspirant salts in the gel sticks of the present invention. By "enhanced efficacy antiperspirant salts" is meant antiperspirant salts which, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 or higher. Any suitable HPLC technique may be employed provided that it is capable of resolving the Al component into five peaks. The enhanced efficacy (or activated) antiperspirant salts are well-known in the industry and are commercially available from several suppliers.

To incorporate the antiperspirant salt in the gel stick composition, it is preferred that the salt is first solubilized or dissolved in a portion of the liquid vehicle. Accordingly, it is preferred to utilize polyhydric alcohol solutions of antiperspirant salts. Especially preferred are solubilized salts which have been partially neutralized by addition of a pH-raising agent to a pH of about 4.1 to 5.0, preferably about 4.3 to 4.8. Particularly preferred neutralized antiperspirant salts are those which contain an additional alkaline glycinate, such as sodium, potassium, or zinc glycinate. Such solubilized antiperspirant salts are described in U.S. Pat. No. 5,643,558, and in U.S. Pat. No. 5,463,098, the disclosures of which are incorporated herein by reference. An example of such a solubilized salt, which is partially neutralized with zinc glycinate, is Westchlor A2Z 8106 (Westwood Chemical Corp.). The preparation of a preferred solubilized antiperspirant salt is described in Example 1 below.

The additional alkaline glycinate which is preferably included in the solubilized antiperspirant salt raises the pH of the antiperspirant salt and, as a result, reduces the degradation of the dibenzylidene alditol in the gel stick. It is generally preferred to add sufficient alkaline glycinate to the solubilized antiperspirant salt so as to raise the pH of an approximately 10% aqueous solution of the antiperspirant salt to about 4.1 to 5.0, preferably about 4.3 to 4.8. (The 10% aqueous solution may be an approximately 50:50 polyhydric alcohol:water solution.) Preferred gel sticks which include such a partially neutralized salt will have a pH greater than 4.4, preferably about 4.7 to about 5.5, and more preferably about 4.8 to about 5.3. The pH of the finished stick can be measured by dissolving one part stick in ninety-nine parts water. The pH of the solubilized antiperspirant salt or of the resulting stick can, of course, be adjusted to the aforementioned preferred pH ranges with any pH-raising agent, or combination of pH-raising agents, provided that the agent or agents selected are soluble in the vehicle and do not adversely affect the clarity or odor characteristics of the stick to a significant extent.

Sufficient antiperspirant salt should be dissolved in the liquid vehicle so that the final composition, after all components are added, includes between about 3% and about 22%, preferably between about 6% and about 15%, of the antiperspirant salt by weight. It should be noted that reference throughout this application to weight percent of antiperspirant salt is intended to be calculated in accordance with the standard industry method, which includes bound water and glycine. This calculation compares with the new U.S.P. method, which excludes bound water and glycine, as follows:

| SALT | STANDARD METHOD | USP METHOD |
|---|---|---|
| Al—Zr—Gly in Prop. Glycol (Ex. 1) | 30% | 22% |
| Al—Zr—Gly in stick (Ex. 2) | 11% | 8.6% |

The gel stick of the present invention will preferably include a chelating agent to improve its color and clarity. Examples of chelating agents include EDTA (ethylenediaminetetraacetate) salts such as $Na_4EDTA$ and $Na_3EDTA$; 1hydroxyethylethylenediaminetriacetate (HEDTA); diethylenetriaminepentaacetate (DTPA); nitrilotriacetate (NTA); ethanoldiglycine disodium salt (EDG); diethanolglycine sodium salt (DEG); and 1,3-propylenediaminetetraacetic acid (PDTA). All of these are known and commercially available. $Na_4EDTA$ and $Na_3EDTA$ are preferred. The gel sticks generally include between about 0.05% and about 3%, preferably between about 0.1% and about 2%, of the chelating agent by weight. If too little chelating agent is included, the stick may have less clarity, an undesirable odor, and/or undesirable yellowness. If too much chelating agent is included, the clarity and/or other properties of the stick may be adversely affected. The chelating agent may reduce the color (in particular the yellow color) of the stick that can result, for example, from the presence of residual iron (or other metal contaminants) that may be present in the stick from a variety of sources. The gel stick preferably measures 0-1 on the yellowness scale.

The chelating agent may also act as a gelling agent stabilizer by increasing the pH of the stick, thus reducing or eliminating the need for other alkaline gelling agent stabilizers such as NaOH and KOH. The gel sticks preferably are substantially free of NaOH and KOH and, as a result, do not have the odor that can result from the interaction of these materials with the vehicle, particularly with propylene glycol. The elimination of other alkaline gelling agent stabilizers, particularly NaOH and KOH, is an advantageous feature of the present invention and is believed to substantially contribute to the odor-free characteristics of the gel sticks of the present invention.

Suitable emollients may be incorporated into the gel stick to provide it with desirable application properties (smoothness, reduced tack, etc.). Examples of emollients include fatty acid esters such as isopropyl myristate and isopropyl palmitate; diesters of adipic, phthalic, and sebacic acids such as di-n-butyl phthalate, diisopropyl sebacate, diethyl sebacate, and diisopropyl adipate; propylene glycol diesters of short chain fatty acids; nonvolatile silicone oils such as dimethyl siloxane and dimethicone copolyol; volatile silicones such as Dow Corning 344 and Dow Corning 345 (available from Dow Corning), Silicone 7207 and Silicate 7158 (available from Union Carbide), and SF 1202 (available from General Electric); $C_{12}$–$C_{15}$ alcohol benzoates such as Finsolv (available from Finetex, Inc.); fatty alcohols such as cetyl alcohol and stearyl alcohol; alkyl ether derivatives of polyethylene glycols, polypropylene glycols and polypropylene polyethylene glycol copolymers such as PPG-5-Buteth-7, PPG-5-Ceteth-20, PPG-3-1sosteareth-9 and Glycereth-7-Diisononanoate. Many other examples of emollients are known in the art. The gel stick should include a sufficient quantity of emollient to provide the stick with the desired application properties without interfering with the clarity of the product. The preferred emollients should be soluble in the liquid vehicle and form a clear solution therein. The gel stick preferably includes less than about 10%, more preferably less than about 3%, and most preferably between about 0.25% and 1.25%, of emollients by weight.

The fragrances used in the gel stick can be any conventional fragrance that provides the stick with a desired scent. The quantity of fragrance included should be the quantity needed to provide the desired scent. The gel stick generally includes less than about 2.5%, preferably less than about 1.5%, of the fragrance by weight.

The gel sticks can contain other optional conventional ingredients such as humectants, hardeners such as waxes, fillers, colorants, preservatives, bacteriocides, UV absorbers, and the like. Obviously such materials should be selected so as not to adversely affect the clarity of the stick.

The gel sticks of the present invention may be prepared by the conventional two-phase procedure known in the art. That is, a first phase containing a portion of the vehicle and the gelling agents is heated to a temperature sufficient to dissolve the gelling agents (typically about 110° C.), then cooled to about 100° C. A second phase containing a portion of the vehicle and the remaining ingredients is prepared and heated to about 60° to 70° C., then added to the first phase. The combined mixture is poured into stick form molds and cooled to solidify. A preferred alternative method of preparation is to combine all of the ingredients at a temperature of less than 50° C. with sufficient mixing to form a uniform dispersion (the dibenzylidene alditol is not soluble at room temperature; the hydroxyalkyl cellulose may be predissolved in a portion of the vehicle prior to blending). Portions of this dispersion are then flash heated to a temperature sufficient to dissolve the dibenzylidene alditol, then the resulting solution is poured into stick form molds and cooled to solidify. Ideally, no portion of the solution will be kept at a temperature in excess of 90° C. for more than a few minutes. This preferred process is described more fully in a copending application entitled "One-Phase Process For Making A Clear Antiperspirant Stick Containing Dibenzylidene Alditol" (Docket No. T-649) filed on Feb. 6, 1996 as U.S. Ser. No. 08/588,619 pending, the disclosure of which is incorporated herein by reference.

The following specific examples further illustrate the invention:

EXAMPLE 1

Antiperspirant Salt

A 50% sodium glycinate solution was prepared by mixing 171 lbs. (77.6 kg) 50% NaOH with 67.8 lbs. (30.8 kg) water, then adding 160.3 lbs (72.8 kg) of glycine (1:1 mole ratio of glycine to NaOH), the temperature rising from 25° to 30° C., then from 30° to 35° C., after the first and second additions respectively. To 103.3 lbs. (46.9 kg) of propylene glycol was added 7.8 lbs. (3.5 kg) of 50% sodium glycinate and the solution mixed for ten minutes. To this solution was added 33.9 lbs. (15.4 kg) of zirconium hydroxychloride glycinate (50% aqueous ZHC-gly solution with a Zr:gly ratio of about 1:1 ). After mixing this solution for about ten minutes, 255 lbs. (115.8 kg) of 10% ACH' solution (prepared by heating 10% ACH at about 80° C. for about 16 to 17 hours) was added and mixed for about ten minutes. This solution was preheated to about 70° to 75° C. and fed continuously to a type JHE flash evaporator (APV Crepaco Inc., Tonawanda, N.Y.; evaporator modified by mounting to the top of the flash chamber a 3 foot rectification tower filled with about 2.5 feet of 0.5 inch ceramic Bed saddles) maintained at about 60 mm Hg (absolute pressure) from which was withdrawn at about 1 gal/hr a clear solution comprising 65% propylene glycol, 30% enhanced efficacy aluminum-zirconium tetrachlorhydrate-glycine (more than 80% of aluminum in peaks 3 and 4 with peak 4 to peak 3 area ratio greater than 1 and Gly:Zr ratio about 1.6:1), and 5% water. The pH of a sample of this solution diluted with an equal portion of distilled water was about 4.7. This antiperspirant salt solution is incorporated into the following examples.

EXAMPLES 2 AND 3

| Ingredient | Ex. 2 Wt. % | Ex. 3 Wt. % |
| --- | --- | --- |
| Propylene glycol | 85.50 | 84.70 |
| Al/Zr tetrachlorohydrate-gly | 11.00* | 11.00* |
| Dibenzylidene sorbitol | 1.00 | 1.30 |
| Hydroxypropyl cellulose | 0.30 | 0.30 |
| Fragrance | 1.25 | 1.25 |
| Diisopropyl sebacate | — | 1.00 |
| Glycereth-7-diisononanoate | 0.50 | — |
| Dimethicone copolyol (ABIL B 8851) | 0.25 | 0.25 |
| Na₄EDTA | 0.20 | 0.20 |

*Weight % of salt in final composition. Salt is added in solubilized form as prepared in Example 1.

Examples 2 and 3 were prepared according to the following procedure.

Phase A

About 65% of the total propylene glycol mass (excluding that which is part of the antiperspirant salt solution) is added to an appropriately sized vessel. Hydroxypropyl cellulose is added and stirred well to dissolve. After heating this solution to 110°–115° C., the dibenzylidine sorbitol is added with stirring until completely dissolved. This Phase A solution is then cooled to about 100° C.

Phase B

About 35% of the total propylene glycol mass (excluding that which is part of the antiperspirant salt solution) is added to an appropriately sized vessel, stirred and heated to about 60°–70° C. The Na₄EDTA is added and mixed well. The Al/Zr tetrachlorohydrate-gly solution (as prepared in Example 1) is added and the solution mixed well until it becomes clear and homogeneous. The emollients (i.e. diisopropyl sebacate or glycereth-7-diisononanoate and the dimethicone copolyol) are then added and the Phase B solution is mixed well until clear.

Combined Phase

Phase B is added to phase A with mixing and cooled to about 80° C. The fragrance is added and allowed to mix well. The product is poured into suitable stick containers and cooled to solidify.

| Ingredient | Ex. 4 Wt. % | Ex. 5 Wt. % |
| --- | --- | --- |
| Propylene glycol | 86.00 | 85.65 |
| Hydroxypropyl cellulose | 0.30 | 0.20 |
| Dibenzylidene sorbitol | 0.50 | 0.95 |
| Al/Zr tetrachlorohydrate-gly | 11.00* | 11.00* |
| Na₄EDTA | 0.20 | 0.20 |
| Glycereth-7-diisononanoate | 0.50 | 0.50 |
| Dimethicone copolyol (ABIL B 8851) | 0.25 | 0.25 |
| Fragrance | 1.25 | 1.25 |

*Weight % of salt in final composition. Salt is added in solubilized form as prepared in Example 1.

Examples 4 and 5 are prepared by procedures analogous to the procedure used to prepare examples 2 and 3.

| Ingredient | Wt. % |
| --- | --- |
| Propylene glycol | 84.85 |
| Hydroxypropyl cellulose | 0.35 |
| Dibenzylidene sorbitol | 1.10 |
| Al/Zr tetrachlorohydrate-gly | 11.00* |
| Diisopropyl sebacate | 1.00 |
| Dimethicone copolyol | 0.25 |
| Na₄EDTA | 0.20 |
| Fragrance | 1.25 |

Weight % of salt in final composition. Salt is added in solubilized form as prepared in Example 1.

Example 6 is prepared by a procedure analogous to the procedure used to prepare examples 2 and 3.

EXAMPLE 7

| Ingredient | Wt. % |
| --- | --- |
| Propylene glycol | 92.75 |
| Al/Zr tetrachlorohydrate-gly | 3.00* |
| Na₄EDTA | 0.20 |
| Dibenzylidene sorbitol | 1.30 |
| Hydroxypropyl cellulose | 0.50 |
| Oleth-10 | 0.75 |
| PPG-10 butanediol | 0.75 |
| PPG-3 myristyl ether | 0.75 |

Weight % of salt in final composition. Salt is added in solubilized form as prepared in Example 1.

Example 7 is prepared by a procedure analogous to the procedure used to prepare examples 2 and 3.

EXAMPLES 8

| Ingredient | Wt. % |
| --- | --- |
| Propylene glycol | 85.00 |
| Al/Zr tetrachlorohydrate-gly | 11.00* |
| Dibenzylidene sorbitol | 1.20 |
| Hydroxypropyl cellulose | 0.30 |
| Fragrance | 1.25 |
| Diisopropyl sebacate | 1.00 |
| Dimethicone copolyol (ABIL B 8851) | 0.25 |

*Weight % of salt in final composition. Salt is added in solubilized form as prepared in Example 1.

Examples 8 is prepared by a procedure analogous to the procedure used to prepare examples 2 and 3.

What is claimed is:

1. A clear gel cosmetic stick comprising a liquid vehicle, an antiperspirant salt dissolved in said liquid vehicle, a dibenzylidene alditol, and a hydroxyalkyl cellulose, wherein the amount of said dibenzylidene alditol comprises about 1.5% by weight or less.

2. The cosmetic stick of claim 1 comprising in percent by weight about 70% to about 95% of a liquid vehicle comprising a polyhydric alcohol having from 3 to 6 carbon atoms and from 2 to 6 hydroxyl groups, about 3% to about 22% of an antiperspirant salt dissolved in said liquid vehicle, about 0.5% to about 1.5% of a dibenzylidene alditol, and about 0.1% to about 0.5% of a hydroxyalkyl cellulose.

3. The cosmetic stick of claim 2 wherein said cosmetic stick has a pH greater than 4.4 and a turbidity of less than about 120 NTU.

4. The cosmetic stick of claim 2 comprising in percent by weight about 75 to 92% of said liquid vehicle, about 6% to 15% of said antiperspirant salt, about 0.7% to 1.3% of said dibenzylidene alditol, and about 0.2% to 0.4% of said hydroxyalkyl cellulose.

5. The cosmetic stick of claim 4 wherein said cosmetic stick has a pH of about 4.8 to about 5.3, a turbidity of less than about 100 NTU, and a hardness of about 60 to 150.

6. The cosmetic stick of claim 2, 3, 4 or 5 wherein said dibenzylidene alditol comprises dibenzylidene sorbitol.

7. The cosmetic stick of claim 6 wherein said antiperspirant salt comprises aluminum chlorohydrate, enhanced efficacy aluminum chlorohydrate, aluminum-zirconium chlorohydrate or enhanced efficacy aluminum-zirconium chlorohydrate.

8. The cosmetic stick of claim 7 wherein said polyhydric alcohol comprises propylene glycol.

9. The cosmetic stick of claim 8 wherein said hydroxyalkyl cellulose comprises hydroxypropyl cellulose.

10. The cosmetic stick of claim 2 wherein said liquid vehicle is substantially free of monohydric alcohol.

11. The cosmetic stick of claim 10 wherein said liquid vehicle is substantially free of NaOH and KOH.

12. The cosmetic stick of claim 11 additionally comprising about 0.1% to about 2% of a chelating agent.

13. The cosmetic stick of claim 12 additionally comprising less than about 3% of one or more emollients.

14. The cosmetic stick of claim 3 which is stable with respect to clarity and odor when stored at 45° C. for 3 months.

15. A clear gel cosmetic stick comprising in percent by weight 75% to 92% of a liquid vehicle comprising a polyhydric alcohol having from 3 to 6 carbon atoms and from 2 to 6 hydroxyl groups, 6% to 15% of an antiperspirant salt dissolved in said liquid vehicle, 0.5% to 1.5% of a dibenzylidene alditol, and 0.1% to 0.5% of a hydroxyalkyl cellulose.

16. The cosmetic stick of claim 15 wherein said polyhydric alcohol comprises propylene glycol, said dibenzylidene alditol comprises dibenzylidene sorbitol, said antiperspirant salt comprises aluminum chlorohydrate, enhanced efficacy aluminum chlorohydrate, aluminum-zirconium chlorohydrate or enhanced efficacy aluminum-zirconium chlorohydrate, and said hydroxyalkyl cellulose comprises hydroxypropyl cellulose.

17. The cosmetic stick of claim 16 wherein said cosmetic stick has a pH of 4.8 to 5.3, a turbidity of less than about 100 NTU, and a hardness of 60 to 150.

18. The cosmetic stick of claim 17 wherein said liquid vehicle is substantially free of monohydric alcohol.

19. The cosmetic stick of claim 18 wherein said liquid vehicle is substantially free of NaOH and KOH.

20. A clear gel cosmetic stick comprising a liquid vehicle, an antiperspirant salt dissolved in said liquid vehicle, a dibenzylidene alditol, and a co-gellant, wherein the amount of said dibenzylidene alditol comprises about 1.5% by weight or less.

* * * * *